US006095141A

United States Patent [19]

Armer et al.

[11] Patent Number: 6,095,141

[45] Date of Patent: Aug. 1, 2000

[54] METHODS AND APPARATUS FOR DELIVERING AEROSOLIZED MEDICATION

[75] Inventors: Thomas Alex Armer, Ann Arbor; Bryce Burwick Evans, Jackson; Nahed Mohsen Mohsen, Farmington Hills; Richard Matthew Pavkov, Northville, all of Mich.; Atul M. Sudhalkar, Fremont, Calif.

[73] Assignee: Sheffield Pharmaceuticals, Inc., St. Louis, Mo.

[21] Appl. No.: 09/326,531

[22] Filed: Jun. 7, 1999

Related U.S. Application Data

[63] Continuation of application No. 08/954,352, Oct. 17, 1997, Pat. No. 5,954,047.

[51] Int. Cl.[7] .......................... A61M 16/00; A61M 11/00

[52] U.S. Cl. ............................... 128/204.26; 128/200.14; 128/200.23; 128/200.18; 128/204.25

[58] Field of Search ......................... 128/200.23, 203.15, 128/203.12, 200.14, 200.18, 200.21, 204.26, 204.25

[56] References Cited

U.S. PATENT DOCUMENTS

| | | | |
|---|---|---|---|
| 3,236,458 | 2/1966 | Ramis | 128/200.18 |
| 3,385,295 | 5/1968 | Beasley | 128/204.25 |
| 3,456,644 | 7/1969 | Thiel | 128/200.23 |
| 3,522,806 | 8/1970 | Szekely | 128/173 |
| 3,636,949 | 1/1972 | Kropp | 128/173 R |
| 3,658,059 | 4/1972 | Steil | 128/200.21 |
| 4,414,972 | 11/1983 | Young et al. | 128/200.23 |
| 4,429,835 | 2/1984 | Brugger et al. | 239/338 |
| 4,534,343 | 8/1985 | Nowacki et al. | 128/200.23 |
| 4,907,583 | 3/1990 | Wetterlin et al. | 128/203.15 |
| 4,940,051 | 7/1990 | Lankinen | 128/200.18 |
| 5,040,527 | 8/1991 | Larson et al. | 128/200.23 |
| 5,054,477 | 10/1991 | Terada et al. | 128/200.14 |
| 5,060,643 | 10/1991 | Rich et al. | 128/200.23 |
| 5,069,204 | 12/1991 | Smith et al. | 128/200.23 |
| 5,178,138 | 1/1993 | Walstrom et al. | 128/200.23 |
| 5,184,761 | 2/1993 | Lee | 222/402.2 |
| 5,224,472 | 7/1993 | Pesenti et al. | 128/200.23 |
| 5,301,666 | 4/1994 | Lerk et al. | 128/203.15 |
| 5,309,900 | 5/1994 | Knoch et al. | 128/200.14 |
| 5,347,998 | 9/1994 | Hodson et al. | 128/200.23 |
| 5,415,162 | 5/1995 | Casper et al. | 128/203.12 |
| 5,435,297 | 7/1995 | Klein | 128/200.23 |
| 5,458,135 | 10/1995 | Patton et al. | 128/200.14 |
| 5,520,166 | 5/1996 | Ritson et al. | 128/200.14 |
| 5,549,101 | 8/1996 | Trofast et al. | 128/203.15 |
| 5,577,497 | 11/1996 | Mecikalski et al. | 128/203.15 |
| 5,590,645 | 1/1997 | Davies et al. | 128/203.15 |
| 5,598,836 | 2/1997 | Larson et al. | 128/200.23 |
| 5,615,670 | 4/1997 | Rhodes | 128/203.15 |
| 5,617,845 | 4/1997 | Poss et al. | 128/203.15 |
| 5,724,986 | 3/1998 | Jones, Jr. et al. | 239/200.14 |

FOREIGN PATENT DOCUMENTS

| | | |
|---|---|---|
| 363060 A2 | 9/1989 | European Pat. Off. . |
| 839544 A2 | 5/1998 | European Pat. Off. . |
| 2279879 | 1/1995 | United Kingdom . |

*Primary Examiner*—John G. Weiss
*Assistant Examiner*—Todd M. Martin
*Attorney, Agent, or Firm*—Fitzpatrick, Cella, Harper & Scinto

[57] ABSTRACT

A metered dose inhaler (10) for use with a pressurized aerosol canister (18) includes a housing (12) defining a conduit (16) with a mouthpiece (56), and an actuator (26) with a nozzle discharge orifice (30) arranged to discharge aerosol into the conduit. An air tube (34) is arranged within the conduit with an inlet (38) of the air tube formed in the conduit wall (74) and an outlet (36) of the air tube in opposing relationship with the nozzle orifice. Inhalation through the mouthpiece causes air to be drawn into the inlet and flow out of the outlet of the air tube to form an air jet which impinges on an oppositely moving aerosol plume from the orifice. Automatic actuation of the canister responsive to the patient's inhalation is achieved by a canister trigger (154) connected to a movable piston assembly (132) forming a wall of a variable-volume chamber (162) in fluid communication with a venturi (184) in the air tube. Air drawn through the venturi by the user's breath causes evacuation of air from the chamber, thereby moving the piston assembly and trigger to cause actuation of the canister.

8 Claims, 5 Drawing Sheets

METHODS AND APPARATUS FOR DELIVERING AEROSOLIZED MEDICATION

This application is a continuation of U.S. application Ser. No. 08/954,352, filed Oct. 17, 1997, now U.S. Pat. No. 5,954,047.

FIELD OF THE INVENTION

The present invention relates to method and apparatus for delivering a dose of aerosolized medication for inhalation by a patient into the lungs.

BACKGROUND OF THE INVENTION

Aerosols are increasingly being used for delivering medication for therapeutic treatment of the lungs. For example, in the treatment of asthma, inhalers are commonly used for delivering bronchodilators such as $\beta_2$ agonists and anti-inflammatory agents such as corticosteroids. Two types of inhalers are in common use, metered dose inhalers (MDIs) and dry powder inhalers (DPIs). Both types have as their object the delivery of medication, which is typically in the form of a solid particulate or powder, into the airways of the lungs at the location of the condition being treated.

In the MDI device, the medication is provided by the pharmaceutical manufacturer in a pressurized aerosol canister, with the medication being suspended or dissolved in a liquid propellant such as a chlorofluorcarbon (CFC) or hydrofluroralkane (HFA). The canister includes a metering valve having a hollow discharge stem which can be depressed inward into the canister to discharge a metered volume of propellant-medication mixture in the form of an aerosol comprising fine droplets of propellant in which particles of the medication are suspended or dissolved. A typical MDI for use with such a canister includes a housing having an actuator and nozzle. The canister is inserted into the housing with the hollow discharge stem of the canister being received in a bore in the actuator. Depressing the closed end of the canister causes the stem to be pushed inward into the canister so that a metered volume of medication is discharged through the nozzle. The housing further defines a flowpath in fluid communication with the nozzle, the flowpath having an outlet at a mouthpiece portion of the housing, such that the aerosolized medication may be inhaled after it exists the mouthpiece portion. The patient either inserts the mouthpiece into the mouth with the lips closed around the mouthpiece, or holds the mouthpiece at a slight distance away from an open mouth. The patient then depresses the canister to discharge the medication, and simultaneously inhales.

Existing MDIs suffer from a number of significant disadvantages. One problem with existing MDIs is poor delivery efficiency of the medication. It has been estimated that on average, with existing MDIs, only about 10 percent of the medication does which is dispensed from the canister actually reaches the lungs where it can achieve the intended result.

Poor delivery efficiency is caused by a number of factors. One of these is incomplete evaporation of propellant, resulting in a large portion of the metered does being delivered in a form which cannot be inhaled into the lungs. For effective delivery of aerosolized medication to the airways of the lungs, it is desirable that most of the particles which are inspired be less than about 10 microns (one micron=one-thousandth of a millimeter) in size, and preferably between about 1 micron and 5 microns. Incomplete evaporation of propellant at the outlet of the mouthpiece results in a substantial fraction of the metered dose being delivered in the form of relatively large liquid droplets instead of fine dry particles and/or vapor. Such droplets cannot be inspired, but rather tend to impact the inside of the mouth and at the back of the patient's throat, with the result that much of the medication is swallowed. The local concentration of medication in the mouth and throat can cause local immunosuppression response, as well as development of fungal infections in the case of corticosteroids. Additionally, swallowing $\beta_2$ agonists causes relaxation of the smooth muscles of the gastrointestinal tract, which decreases contractility and activity of the stomach. Further, the wasted medication has been estimated to cost U.S. patients about $750 million per year.

Another factor contributing to the problem of poor delivery efficiency is high linear velocity of the aerosol as it exits the mouthpiece, which tends to lead to impaction of the aerosol in the mouth and throat. Ideally, the velocity of the aerosol should match the velocity of the patient's inspired breath so that the particles are entrained in the breath and carried into the lungs. With many existing MDIs, the exit velocity of the aerosol substantially exceeds the velocity of the patient's breath. The high-velocity plume strikes the back of the throat, causing impaction and sticking.

Yet another factor contributing to the poor delivery efficiency of existing MDIs is excessive length of the plume or bolus of aerosol exiting the device. In existing MDIs, this length typically exceeds 25 centimeters, which makes it difficult for the patient to inhale the entire bolus.

In an effort to decrease plume velocity, some MDI designers have added tubular spacers between the aerosol nozzle and the mouthpiece. Although spacers improve delivery efficiency, most of the drug which is discharged from the nozzle impacts and sticks on inner surfaces of the spacer, and is therefore unavailable for inhalation by the user. Thus, MDIs wit spacers still suffer from unacceptably low delivery efficiencies.

Furthermore, although dry powder inhalers inherently avoid some of the aforementioned problems of MDIs, such as excessive aerosol velocity, DPIs still suffer from the problem of impaction and sticking of medication on the inner surfaces of the devices, particularly under certain environment conditions such as high relative humidity, which tends to cause particle aggregation.

Another problem with existing MDIs is the difficulty patients have in coordinating their inhalation with the discharge of the aerosol. In manually operated MDIs, patients frequently inhale too early or too late to effectively inspire the medicaiton. Although a number of breath-actuated MDIs have been devised to address this problem, most of these devices cause discharge at the very onset of the patient's inspiratory effort. Depending on the lung condition being treated and its location, it may often be more desirable for he medication to be discharged near the peak of the patient's inhalation rather than the beginning. Further, it may be desirable to be able to selectively vary the point in the patient's inhalation at which medication is discharged in order to tailor the location of drug delivery to the condition being treated. These advantages are not possible with existing MDIs.

Accordingly, it has been an object of the present invention to provide a method and apparatus for delivering an aerosolized medication in which the respirable fraction of the metered dose (i.e., fraction in he form of dry particles of the optimum size) is maximized at the exit of the apparatus.

It has been a further object of the present invention to provide a method and apparatus for delivering an aerosolized medication in which the linear velocity of the aerosol at the exit of the apparatus approximately matches the velocity of he patient's inspired breath.

It has been another object of the invention to maximize dispersion and mixing of the drug particles in the bolus of an aerosol within an inhaler apparatus.

It has been a still further object of the present invention to provide a method and apparatus for delivering an aerosolized medication in which the length of the bolus of aerosolized medication which exits the apparatus is as short as possible.

A further object of the invention has been to provide a method and apparatus for maximizing the evaporation of liquid propellant in an inhaler.

Still another object of the invention has been to provide a method and apparatus for delivering an aerosolized medication in which impaction and sticking of medication on the inner walls of the apparatus is minimized.

It has been another object of the present invention to provide a method and apparatus for delivering an aerosolized medication in which the discharge of medication is synchronized with the patient's inspired breath, and in which the timing of the discharge in relation to the patient's breath can be selectively varied.

SUMMARY OF THE INVENTION

The above and other objects of the invention are achieved by the methods and apparatus of the invention in which flow control techniques and devices are used to promote mixing of the propellant-medication mixture with air to increase evaporation of propellant, to slow down the aerosol plume before it reaches the exit of the apparatus, and to reduce the impaction of aerosol on the inner walls of the apparatus. The invention also provides an apparatus and method for synchronizing the actuation of the canister with the patient's inspiratory effort exerted on the mouthpiece of the apparatus.

More specifically, the invention provides a metered does inhaler apparatus including a housing adapted to support a pressurized canister, the housing having an actuator and nozzle assembly with a bore adapted to receive the hollow outlet stem of the canister, the housing further including a generally tubular conduit having an open end forming a mouthpiece adapted to be inserted into the mouth of a user, a nozzle discharge orifice of the actuator and nozzle assembly being positioned to direct a plume of aerosolized medication into the conduit; and an air tube supported within the conduit and having an air tube outlet arranged opposite the nozzle discharge orifice and an air tube inlet in fluid communication with ambient air outside the conduit, the air tube being oriented so that air flowing out of the air tube outlet is directed so as to impinge on a plume of aerosolized medication discharged from the canister through the nozzle discharge orifice. Thus, an inspiratory effort exerted on the mouthpiece causes air to flow into the air tube inlet and out the air tube outlet to impinge on the plume and thereby enhance dispersion and mixing of the medication within the conduit. The air jet from the air tube also causes the plume to slow down so that the velocity of the aerosol exiting the device approximately matches the velocity of a patient's inspired breath. Slowing down the plume also increases the residence time of the aerosol within the apparatus and leads to a shorter bolus to be inhaled. The increased mixing and residence time promote more complete evaporation of propellant at the exit of the mouthpiece.

In one embodiment of the invention, the apparatus is configured so that the nozzle discharge orifice directs a plume toward the open end of the mouthpiece. The air tube is arranged to direct an air jet away from the open end of the mouthpiece so as to impinge on the plume. The air tube is supported within the conduit by one or more hollow spokes connected to the wall of the conduit, with the hollow passage of each spoke being connected atone end to a corresponding passage through the conduit wall to ambient air outside the conduit and at the other end to the inlet of the air tube. When the patient inhales on the open end of the mouthpiece, air is drawn into the air tube to cause an air jet to exit the air tube. Once this air jet has been established, the canister is actuated to discharge a plume of aerosol toward the air jet. The plume and air jet meet, causing mixing and deceleration of the plume.

In another embodiment of the invention, the nozzle is positioned to direct a plume away from the open end of the mouthpiece toward the far end of the conduit, which end is substantially closed by an end wall. The air tube is mounted on the end wall, with the inlet of the air tube connected to a passage through the end wall to ambient air outside the conduit. Inhalation by a patient on the open end causes air to be drawn through the air tube in a direction toward the patient's mouth. Once the air jet from the air tube has been established, the canister is activated to direct a plume toward the closed end of the conduit. The air jet and plume meet, causing mixing and deceleration of the plume. The plume must reverse direction before exiting the mouthpiece, so that the same length of conduit is used twice, thereby further increasing residence time of the aerosol within the device.

To reduce impaction and sticking of medication on the inner walls of the apparatus, the invention provides an aerosol flow control apparatus, useful for either MDI or DPI devices, including a housing defining a conduit, the conduit having an open end defining a mouthpiece and a substantially closed end defined by an end wall remote from the mouthpiece, with a medication dispenser assembly being arranged within the housing to direct medication into the conduit. The medication dispenser may be a pressurized canister with actuator and nozzle, or alternatively may be a dispenser for a medication in dry powder form. The end wall includes a plurality of auxiliary air inlets in fluid communication with ambient air outside the conduit, the auxiliary air inlets opening into the conduit adjacent the inner wall of the conduit, in a direction generally toward the open end of the mouthpiece. The conduit further includes a plurality of vortex generators mounted on the inner wall thereof downstream of the auxiliary air inlets, the auxiliary air inlets and vortex generators cooperating to establish a turbulent airflow along the inner wall of the conduit upon an inspiratory effort being exerted on the mouthpiece. The auxiliary air flow acts as a buffer or boundary layer flow along the inner walls of the conduit, reducing the liklihood of aerosol droplets or dry particles impacting and permanently sticking to the inner walls. The vortex generators preferably comprise inwardly directed vanes which are oriented at an angle to the axial direction so as to impart swirl and vorticity to the air flowing over them.

The invention further provides an aerosol flow control apparatus for use with a pressurized canister of medication, in which discharge of the aerosol plume is caused by the patient's inspiratory effort, with the timing of the discharge in relation to the inhalation being selectively variable. To these ends, the apparatus includes a housing adapted to support the canister between a first position in which the discharge stem of the canister is in an inoperative position to a second position in which the discharge stem is in an operative position for discharging a metered volume of medication, the housing further including an outlet through which a user can inhale, the outlet defining a primary air passage. A canister restraint is arranged in the housing and is movable from a rest position in which relative movement between the canister body and discharge stem is prevented to a discharge position in which such movement is permitted. The canister restraint forms a part of, or alternatively is attached to, a device such as a bellows or a movable diaphragm piston assembly which defines a variable-volume chamber. The inhaler includes a resilient member which urges the canister into the second position upon movement of the canister restraint into its discharge position. A secondary air passage extends through the housing between the primary air passage and ambient air outside the housing, the secondary air passage including a venturi. The variable-volume chamber is in fluid communication with a throat of the venturi, whereby inhalation of a user through the outlet causes a low pressure in the venturi throat so as to evacuate air from the chamber and thereby cause the canister restraint to move into the discharge position. By appropriate selection of design parameters such as the chamber cross-sectional area, the force exerted by the resilient member on the canister, the venturi size, and the secondary air passage diameter, the device can be designed to cause actuation of the canister near the peak of a patient's inspiratory effort.

The device preferably further includes means for selectively varying the timing of actuation. For instance, the device may include an adjustment screw intruding into the secondary air passage to act as a variable flow restriction. Turning the screw one direction increases the amount of flow restriction, such that for a given inspiratory rate through the mouthpiece, the amount of time required to evacuate the chamber sufficiently to cause actuation is increased. Conversely, turning the screw in the opposite direction decreases the amount of time required to cause actuation.

These and other objects and advantages of the present invention shall become more apparent from the accompanying drawings and the description thereof.

BRIEF DESCRIPTION OF THE DRAWINGS

The accompanying drawings, which are incorporated in and constitute a part of this specification, illustrate various embodiments of the invention and, together with the general description of the invention given above and the detailed description given below, serve to explain the principles of the invention.

DETAILED DESCRIPTION OF THE DRAWINGS

Figure 1:
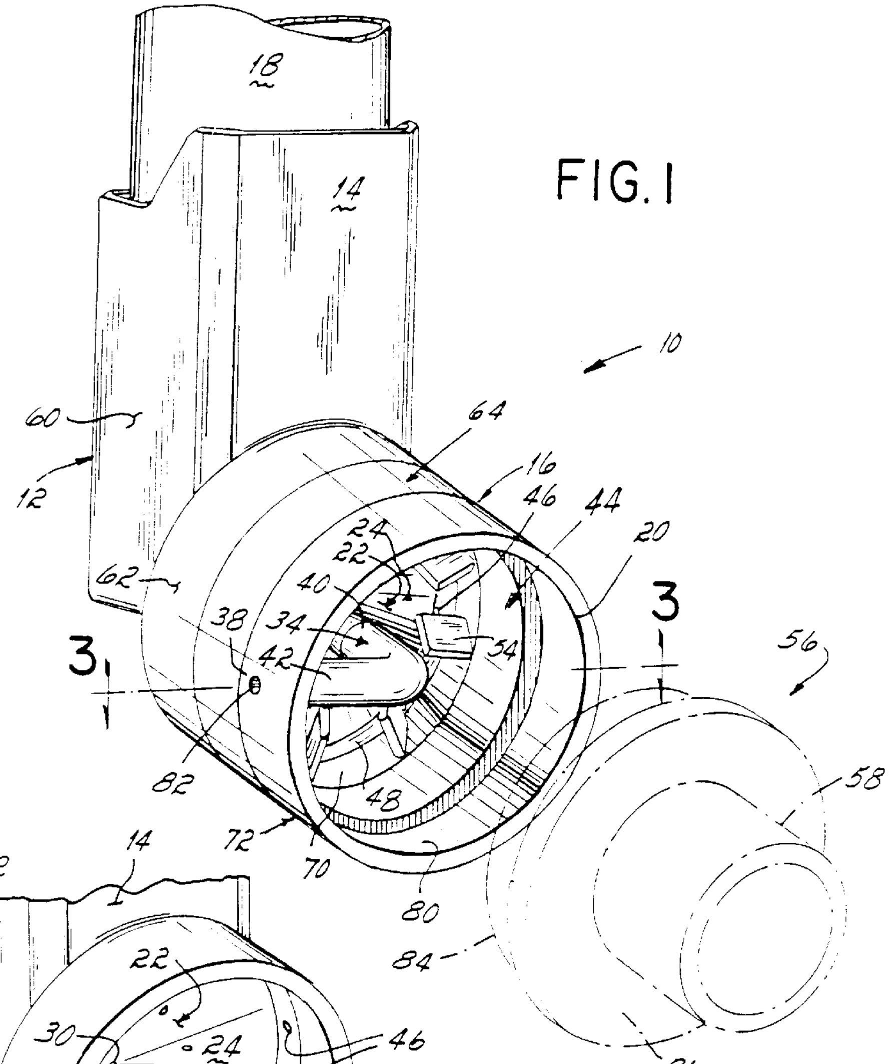
FIG. 1 is a perspective view of an inhaler in accordance with the principles of the present invention.
Figure 2:
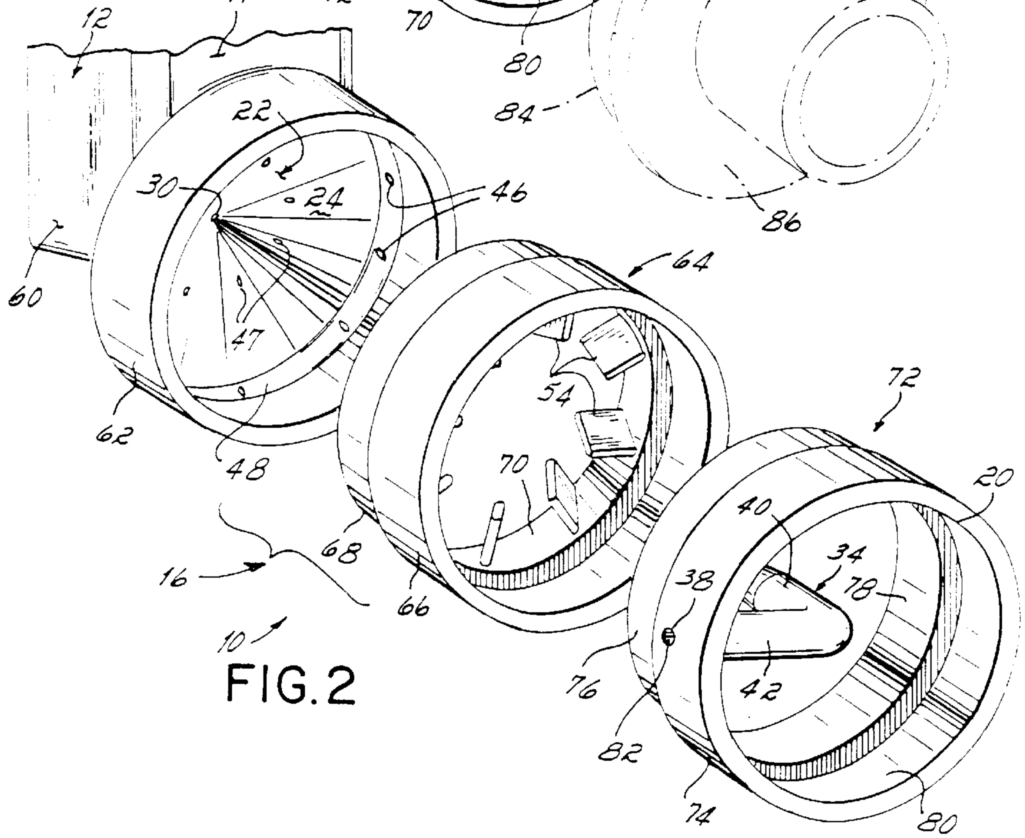
FIG. 2 is an exploded view of the inhaler of FIG. 1.
Figure 3:
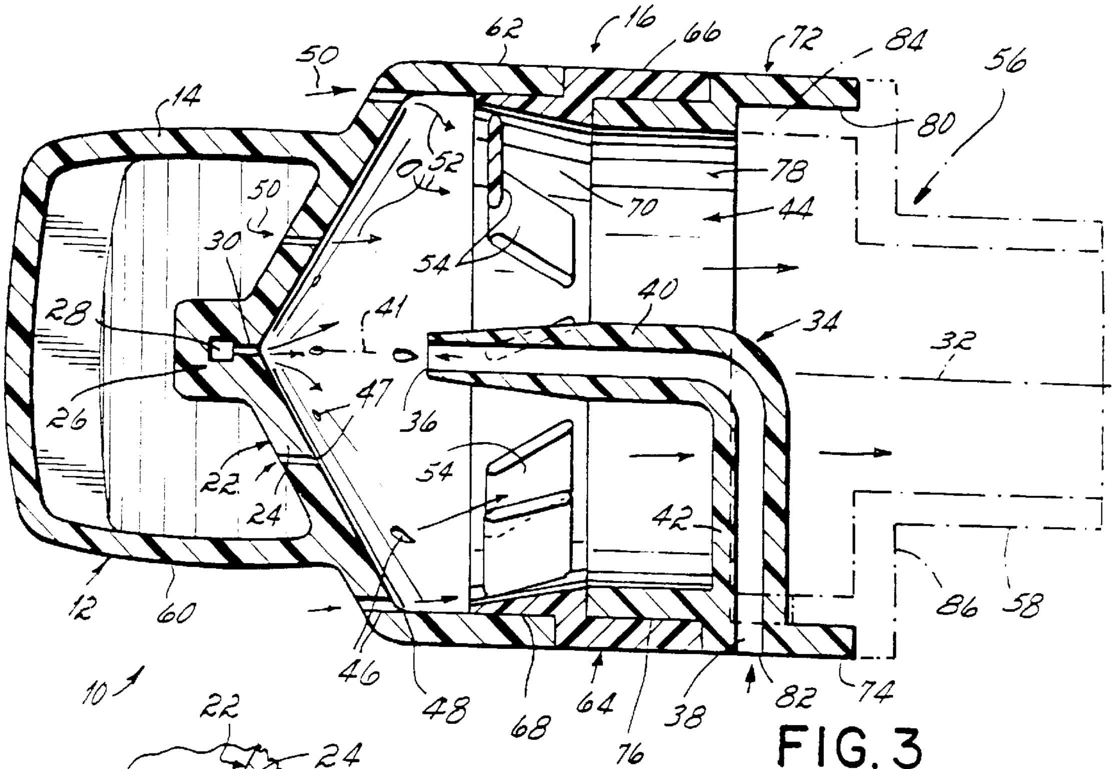
FIG. 3 is a cross-sectional view of the inhaler taken along lines 3—3 of FIG. 1.

FIGS. 1–3 depict a first embodiment of an inhaler 10 in accordance with the principles of the invention. The inhaler 10 includes a housing 12 which has a receptacle portion 14 connected to a conduit 16. The receptacle portion 14 is in the form of a sleeve adapted to receive a standard pressurized canister 18 containing a medication. The canister 18 forms no part of the present invention. The inhaler apparatus of the present invention is usable with any standard pressurized canister having an internal metering valve with a hollow discharge stem which may be depressed inwardly with respect to the canister body from an inoperative position in which discharge of medications is prevented, to an operative position in which a metered volume of the canister contents is discharged through the hollow discharge stem.

The conduit 16 includes an open end 20 spaced from the receptacle portion 14, and a closed end 22 defined by an end wall 24 which is connected to the receptacle portion 14. The end wall 24 preferably is generally conical or hemispherical in shape, with an apex of the end wall 24 forming the portion of the end wall 24 farthest from the open end 20.

With reference to FIG. 3, the housing 12 further includes an actuator and nozzle assembly 26 supported by the end wall 24. The actuator and nozzle assembly 26 includes a bore 28 which is adapted to receive the hollow discharge stem (not shown in FIGS. 1–3) of the canister 18, and a nozzle discharge orifice 30 in fluid communication with the bore 28. The nozzle discharge orifice 30 is advantageously located at the apex of the end wall 24 and oriented to direct an aerosol plume generally along the central longitudinal axis 32 of the conduit. The orifice 30 preferably has an internal diameter at the exit of less than about 0.025 inch, and more preferably between about 0.005 inch and about 0.019 inch.

Thus, upon the canister 18 being depressed in the downward direction in FIG. 1, a metered volume of medication will be discharged into the bore 28 and out the orifice 30 to form a generally conical plume of aerosolized medication within the conduit 16, directed generally toward the open end 20 thereof. The inhaler 10 includes features which promote dispersion and mixing of the aerosolized medication with air within the conduit to enhance evaporation and decrease the velocity of the liquid propellant discharged from the canister 18. More specifically, the inhaler 10 includes an air tube 34 supported within the conduit 16. The air tube 34 has an outlet 36 which is spaced downstream of and in opposing relationship with the nozzle discharge orifice 30, and an inlet 38 which is in fluid communication with ambient air outside the conduit 16. In the embodiment shown in FIGS. 1–3, the air tube 34 is a bent tube which has a generally axial portion 40 which is generally aligned along the conduit's longitudinal axis 32, and a generally radial portion 42 which is attached to the inner wall 44 of the conduit 16. When a user exerts an inspiratory effort on the open end 20 of the conduit 16, air is drawn from outside the conduit 16 into the air tube inlet 38, exiting the air tube outlet 36 in a direction toward the nozzle discharge orifice 30. The portion 40 of air tube 34 is located and oriented within the conduit 16 so that air flowing out from the outlet 36 will impinge on a plume of aerosol exiting the nozzle orifice 30. Once this air flow from the tube 34 has been established, the metering valve of the canister 18 is actuated to discharge a plume of aerosolized medication from the orifice 30. The impingement of air from air tube 34 on the plume causes the plume to slow down and be dispersed so as to occupy a larger portion of the cross section of the conduit 16. The result is enhanced mixing of the aerosol with air, which promotes more complete evaporation of liquid propellant by the time the aerosol bolus exits he open end 20 of the conduit 16, and a reduction in velocity of the plume exiting the open end 20 so that it approaches the velocity of the inspiratory breath. Accordingly, a greater fraction of the metered does of medication dispensed from the cansister 18 exits the open end 20 in the form of respirable dry particles of the optimum size of about one to five microns moving at a relatively low velocity that substantially matches the inspiratory breath velocity, as opposed to relatively large liquid droplets moving at a relatively high velocity. Impaction and sticking of medication within the mouth and throat are thereby reduced.

The air tube 34 and conduit 16 can be integrally formed of one piece, with the internal passage of the air tube 34 extending through the conduit 16 to establish fluid communication with air outside the conduit 16. Alternatively, the air tube 34 can be formed of a metal tube bent into the appropriate configuration and attached to the conduit 16 at the inlet end 38.

Although the embodiments illustrated in FIGS. 1–3 and 7 show the air tube 34 bent at an angle of 90 degrees with the portion 40 coaxially aligned with the axis 41 (FIG. 3) of the nozzle orifice 30, other arrangements may be used without sacrificing the advantages of the invention. For example, the portion 40 may be arranged at an obtuse angle (i.e., between about 90 degrees and 180 degrees, 180 degrees being defined as exactly opposite to the direction of a plume exiting the orifice 30) to the axis 41 of the nozzle orifice 30, with the portion 40 of air tube 34 being oriented to direct an air jet at the orifice 30. Additionally, the portion 42 which attaches to the conduit wall need not be radial, but can be oriented at an acute or obtuse angle to the conduit wall 44.

The invention further includes features which reduce the likelihood of liquid droplets or dry particles impacting and permanently sticking to the inner walls 24 and 44 of the conduit 16. More particularly, the inhaler 10 includes a plurality of auxiliary air inlets 46 through the end wall 24 and circumferentially spaced therearound at at least two different radii from the nozzle orifice 30. A first circumferential ring of auxiliary air inlets 46 are located adjacent the juncture 48 between the end wall 24 and the inner wall 44 of the conduit 16. A second circumferential ring of auxiliary air inlets 47 are located radially between the juncture 48 and the nozzle orifice 30. An inspiratory effort exerted on the open end 20 of the conduit 16 causes air to flow into the auxiliary air inlets 46 and 47 as indicated by arrows 50, and outward therefrom along the inner wall 44 of the conduit 16 and outward from end wall 24, as indicated by arrows 52. This auxiliary air flow forms a buffer or boundary layer air flow along the inner wall 44 and end wall 24 which tends to reduce the impaction and permanent sticking of mediation on inner wall 44 and end wall 24.

To the further attainment of this end, the inhaler 10 also includes a plurality of vortex generators or vanes 54 (best seen in FIG. 2) mounted on the inner wall 44 of the conduit 16 and extending inwardly therefrom. The vanes 54 are located downstream of the auxiliary air inlets 46, with each vane 54 advantageously being located approximately in axial alignment with one of the auxiliary air inlets 46. The vanes 54 are oriented at an angle to the axial direction defined by longitudinal axis 32, so that vorticity and swirl are imparted to air flowing over them. Thus, the boundary layer air flow created by auxiliary air inlets 46 encounters the vanes 54, which impart vorticity and swirl to the boundary layer air flow. This vorticity and swirl further reduce the likelihood of aerosol droplets or particles impacting and permanently sticking to the inner wall 44.

As shown in FIGS. 1 and 3, the inhaler 10 includes a separate mouthpiece 56 which connects to the open end 20 of the conduit 16. The mouthpiece 56 has a reduced diameter portion 58 adapted to be inserted into the mouth of a user of the inhaler 10. After completely exhaling, the user inserts the portion 58 into the mouth with the lips closed around the portion 58, and then begins to inhale, which establishes air flow from the air tube 34 and through the auxiliary air inlets 46. Once these airflows are established and while continuing to inhale, the user depresses the canister 18 to discharge a metered volume of medication and propellant mixture from the nozzle discharge orifice 30. The user continues to inhale to fill the lungs to their capacity, and then typically holds the breath for a period of time to allow the aerosolized medication to settle within the airways of the lungs.

As shown in FIGS. 1–3, the housing 12 is formed in four sections (including the mouthpiece 56) which telescopingly fit together. However, for ease of manufacturing, the housing 12 may alternatively be formed in fewer than four sections. For example, the housing 12 may be formed in two sections, a first section including the receptacle portion 14, end wall 24, and the conduit 16 up to and including the vanes 54, and a second section including the portion of conduit 16 having the air tube 34 and the mouthpiece 56. Alternatively, the housing 14 may be formed in two sections split on a longitudinal plane through the conduit, the two sections being generally mirror images of each other which are joined together along the plane of symmetry. Nevertheless, for illustration purposes, an embodiment having four sections is shown and described.

A first section 60 includes the receptacle portion 14, the end wall 24 and actuator and nozzle assembly 26, and a generally cylindrical portion 62 which forms a part of the conduit 16 and is connected to the end wall 24 at the juncture 48. The first section 60 advantageously is integrally formed of one piece, although it may alternatively be formed in multiple pieces which are subsequently joined together.

A second section 64 includes a second generally cylindrical portion 66 whose inner and outer diameters are equal to those of the first generally cylindrical portion 62, and a reduced-diameter portion 68 which is telescopingly received within the downstream open end of first cylindrical portion 62. The portion 68 has an inner wall 70 which is generally conical, converging slightly in the axial direction toward the mouthpiece 56. The vanes 54 are mounted on the inner wall 70. Second section 64 preferably is integrally formed on one piece, although it may alternatively be formed in multiple pieces which are subsequently joined.

A third section 72 of the housing 12 includes a third generally cylindrical portion 74 whose inner and outer diameters are equal to those of the second generally cylindrical portion 66, and a reduced diameter cylindrical portion 76 which is telescopingly received within the open downstream end of second generally cylindrical portion 66. The outer diameter of portion 76 is approximately equal to the inner diameter of portion 66 so as to provide a tight fit between those parts. The inner surface 78 of portion 76 has a diameter which is approximately equal to the smallest diameter of the conical inner wall 70 so that the juncture between surfaces 70 and 78 does not present any substantial step in the flowpath defined by the conduit 16. The air tube 34 is mounted on the inner surface of the third section 72 at the juncture between the inner surface 78 and the inner surface 80 of third cylindrical portion 74. A hole 82 through the portion 74 mates with the internal passage of air tube 34 to provide fluid communication between the inlet 38 of air tube 34 and ambient air outside the conduit 16. Third section 72 may be integrally formed of one piece or formed in multiple pieces and subsequently joined.

The fourth section of the housing 12 is the mouthpiece 56, which has a generally cylindrical portion 84 which is telescopingly received within the open downstream end of the third generally cylindrical portion 74 (which also defines the open end 20 of the conduit 16). The portion 84 is attached to an annular flange 86, which in turn is attached to the reduced diameter portion 58 which is inserted into a user's mouth. The outer diameter of portion 84 is approximately equal to the diameter of inner surface 80 so as to provide a tight fit therebetween.

The housing 12 advantageously is formed of a plastic such as polyamide, polyester, polyproplene, polyethylene, ABS, polycarbonate, or polyacrylate. The housing 12 may be manufactured by any suitable technique such as injection molding or blow molding.

Figure 3A:
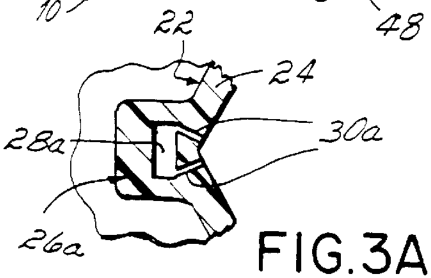
FIG. 3A is a partial cross-sectional view showing an alternative embodiment of the actuator and nozzle of the inhaler.

FIG. 3A shows an alterative embodiment of an actuator and nozzle assembly 26*a* for the inhaler 10, in cross-sectional view on the horizontal plane illustrated in FIG. 3. The actuator and nozzle assembly 26*a* includes two spaced-apart discharge orifices 30*a* which are both fluidly connected to the bore 28*a* and which converge toward each other in the direction of the mouthpiece 56. Thus, depressing the canister 18 so as to discharge a metered volume of medication into the bore 28*a* causes two aerosol plumes to be emitted from the pair of orifices 30*a*. The plumes converge and impinge on each other upstream of the air tube outlet 36, causing the aerosol to spread out, thereby aiding mixing of the aerosol with air. Additionally, impingement of the two plumes aids in creating smaller droplets, which enhances evaporation of propellant. It will be appreciated that for convenience of illustration, the bore 28*a* is shown as being elongated in the horizontal direction and orifices 30*a* are shown as being spaced apart in the horizontal plane. Advantageously, however, the bore 28*a* may simply be extended in the vertical direction and the orifices 30*a* vertically spaced apart and angled toward each other so as to achieve the desired convergence of the two plumes.

Figure 4:
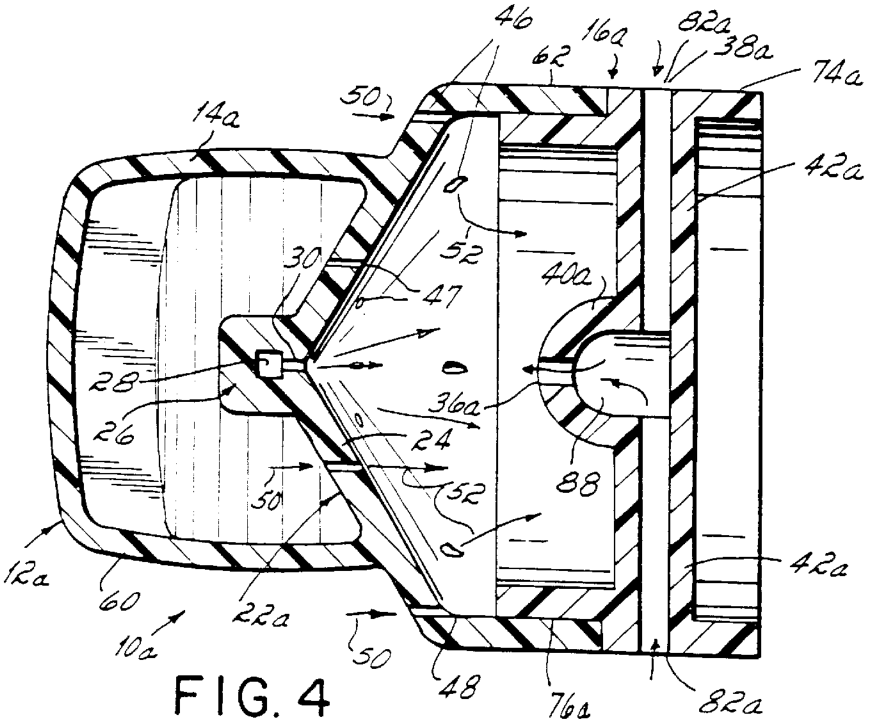
FIG. 4 is a cross-sectional view similar to FIG. 3, showing an alternative embodiment of the inhaler.

FIG. 4 depicts an alternative embodiment of an inhaler 10*a* in which the elongated air tube 34 of inhaler 10 has been replaced by a shorter air tube in the form of a hub 40*a* which is supported in the conduit 16 by a pair of hollow spokes 42*a*. In FIG. 4, parts identified by reference numerals having the letter "a" suffix denote parts analogous to those bearing the same reference numerals without the suffix in FIG. 3, while parts identified with identical reference numbers in FIGS. 3 and 4 denote identical parts. Thus, the hub 40*a* is analogous to the axial portion 40 of the air tube 34, and the spokes 42*a* are analogous to the radial portion 42 of air tube 34. The hub 40*a* includes a central cavity 88 of a first diameter, and an outlet passage 36*a* of a second smaller diameter. The outlet passage 36*a*is generally coaxial with the conduit 16 and oriented so that air flowing outward therefrom is directed toward the nozzle orifice 30. The internal passages of spokes 42*a* are connected to outside air by a pair of holes 82*a* through the cylindrical portion 74*a*. In the embodiment of the inhaler 10*a*shown in FIG. 4, there is no section of the housing analogous to the second section 64 of FIG. 3. Thus, the vanes 54 have been eliminated from the inhaler 10*a*. However, the auxiliary air inlets 46 are still present in the inhaler 10*a* to provide a boundary layer air flow along the inner wall of the conduit 16*a*.

Figure 5:
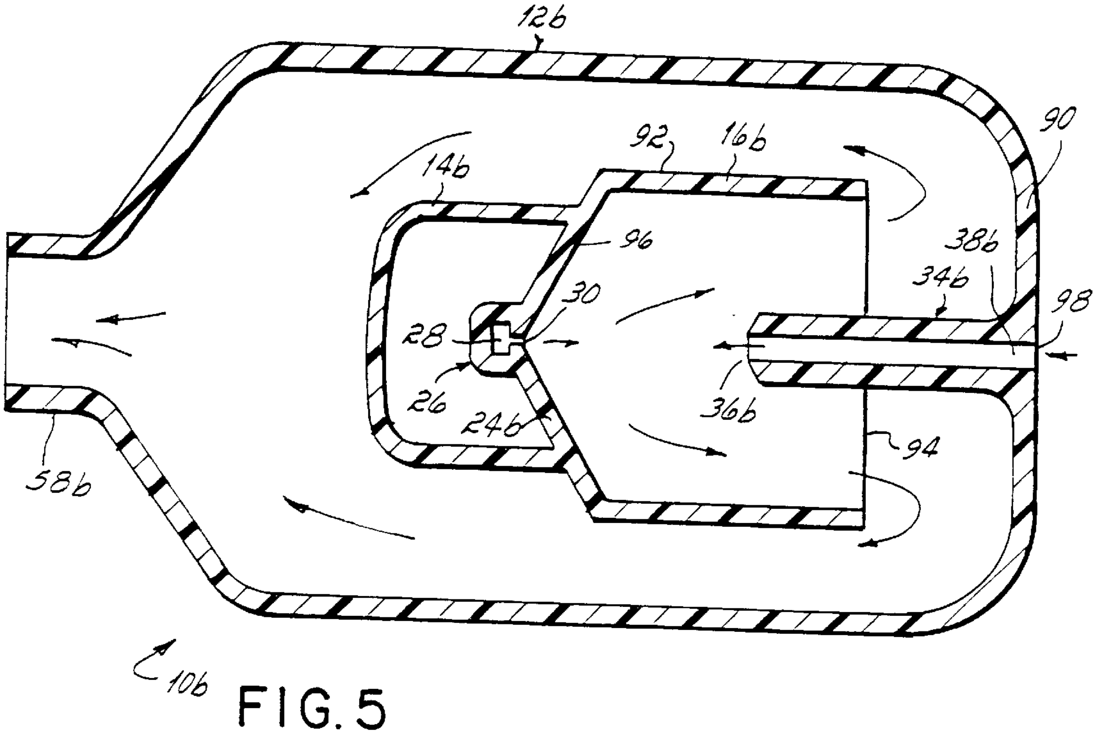
FIG. 5 is a cross-sectional view similar to FIG. 3, showing yet another alternative embodiment of the inhaler.
Figure 6:
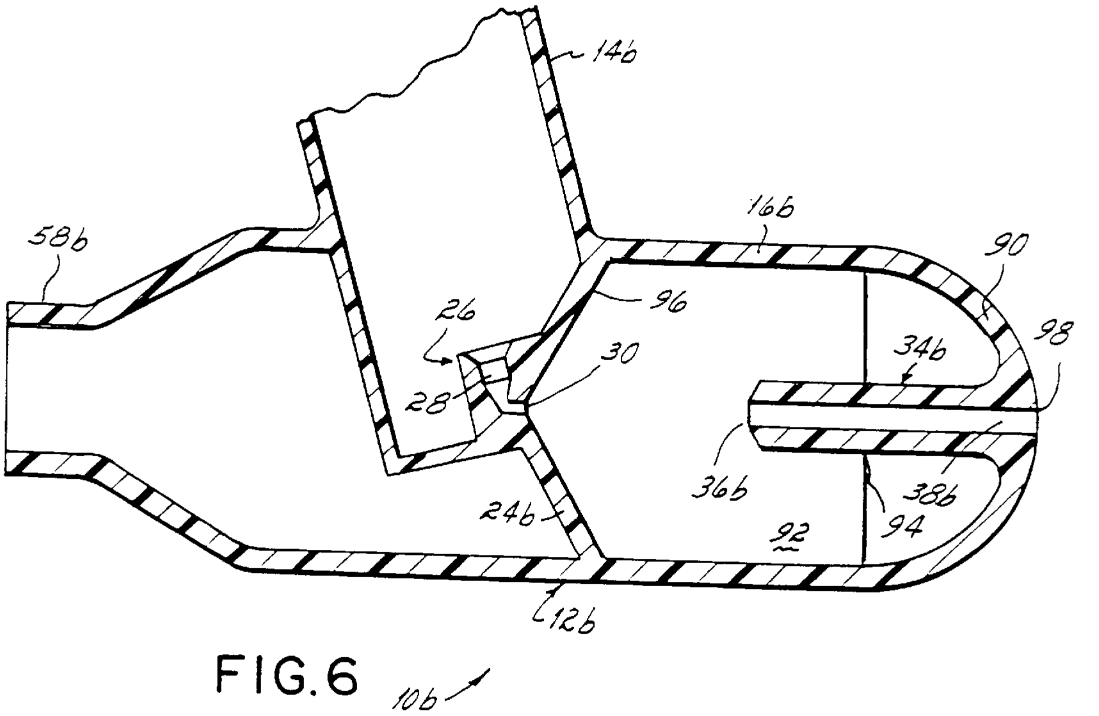
FIG. 6 is cross-sectional view of the inhaler of FIG. 5 taken on a plane normal to that of FIG. 5.

FIGS. 5 and 6 illustrate yet another embodiment of an inhaler in accordance with the principles of the present invention. FIG. 5 schematically depicts a horizontal cross section analogous to FIG. 3, showing an inhaler 10*b* in which the aerosol plume is directed away from the user so that the aerosol must reverse direction before being inspired. FIG. 6 schematically depicts a vertical cross section of the inhaler 10*b*. Again, like parts are denoted by like reference numerals, while analogous parts are denoted by the letter "b" suffix. The inhaler 10*b* includes a housing 12*b* defining a conduit 16*b* which has a first closed end defined by an end wall 90 and a second open end defined by a mouthpiece portion 58*b* adapted to be inserted into a user's mouth. The conduit 16*b* has a first larger internal cross sectional area over the majority of its length, narrowing to a second smaller internal cross sectional area at the mouthpiece portion 58*b*. The housing further includes a receptacle portion 14*b* which penetrates into the conduit 16*b* at a location between the end wall 90 and the mouthpiece portion 58*b*. The receptacle portion 14*b* receives a standard pressurized canister (not shown). The housing 12*b* further includes an actuator and nozzle assembly 26 arranged at the bottom end of receptacle portion 14*b* such that the hollow outlet stem of the canister may be inserted into a bore 28 of the actuator and nozzle assembly 26. The details of the actuator and nozzle assemble 26 have already been described in connection with FIG. 3. The nozzle discharge orifice 30 is oriented so as to direct an aerosol plume toward the end wall 90.

The inhaler 10*b* includes an internal conduit 92 which is coaxially disposed with the conduit 16*b*. The internal conduit 92 has an open end 94 spaced from and adjacent the end wall 90, and a closed end 96 remote from the end wall 90 and defined by an end wall 24*b* which supports the actuator and nozzle assembly 26. The inhaler further includes an air tube 34*b* attached to the end wall 90 and coaxially disposed within the conduit 16*b*. The air tube 34*b* intrudes part way into the inner conduit 92 toward the nozzle discharge orifice 30. The inlet 38*b* of air tube 34*b* is connected to ambient air outside the conduit 16*b* by a hole 98 through end wall 90. The outlet 36*b* of air tube 34*b* is in opposing relation to the orifice 30. Aerosol emitted from the orifice 30 enters into the interior of inner conduit 92 and proceeds toward the end wall 90 of outer conduit 16*b*. Inhalation of the user through the mouthpiece 58*b* causes air to enter through hole 98 into air tube 34*b* and out the outlet 36*b* toward the plume. The plume and the air jet from air tube 34*b* meet, causing the plume to slow down and spread out within inner conduit 92. Continued inhalation by the user causes the dispersed aerosol to exit through the open end 94 of inner conduit 92, and then reverse directions to flow through the space between the inner conduit 92 and the outer conduit 16*b,* and thence through the mouthpiece 58*b*. Thus, the aerosol travels a portion of the length of conduit 16*b* twice, thereby increasing residence time of the aerosol within the device before exiting the mouthpiece 58*b*. This leads to more complete evaporation of liquid propellant. Furthermore, the flow reversal insures that the velocity of the aerosol exiting the mouthpiece will be substantially equal to the velocity of the user's inspired breath, reducing the problem of impaction in the mouth and throat.

Figure 7:
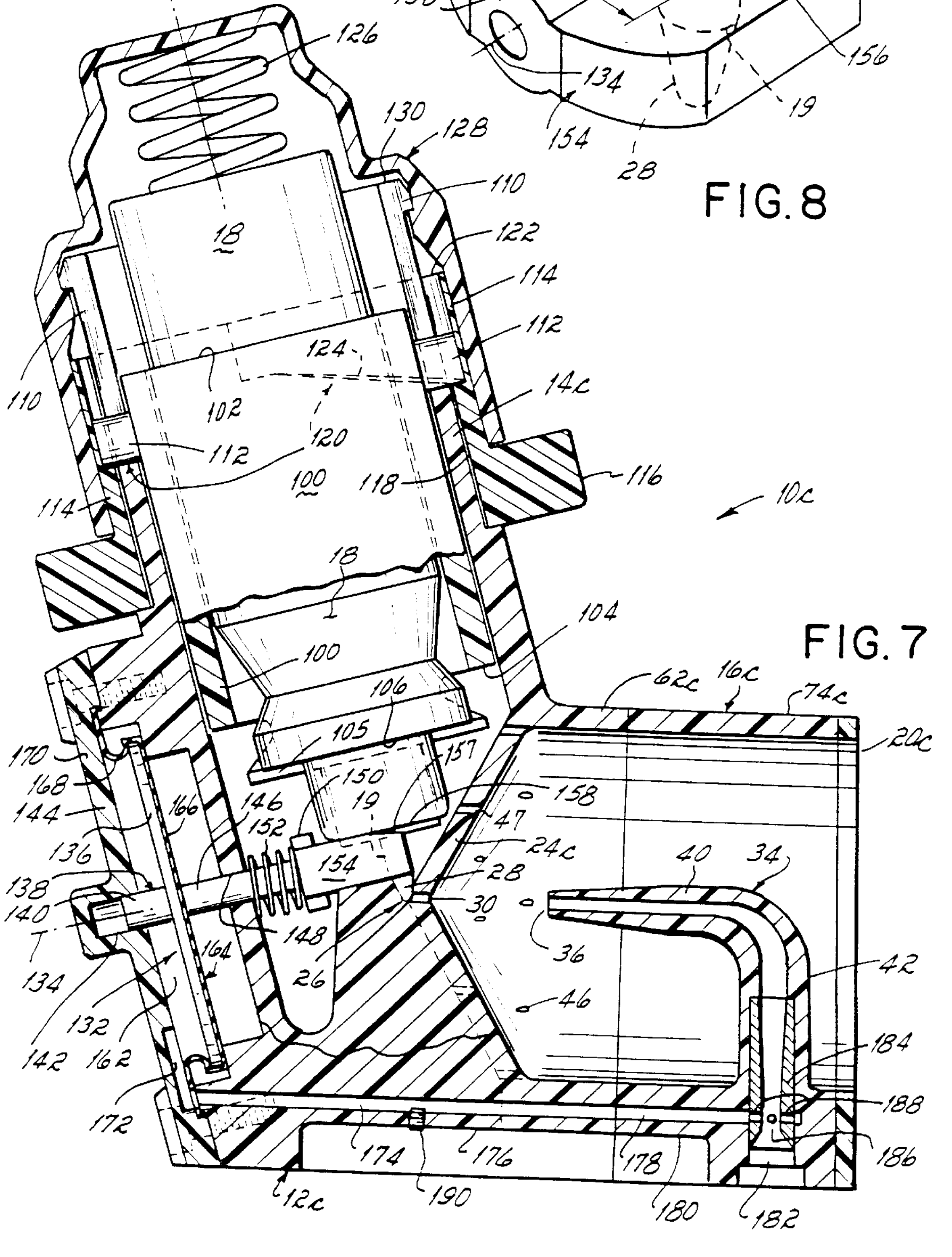
FIG. 7 is a cross-sectional view of still another alternative embodiment of the invention, having features for achieving automatic actuation of a canister responsive to a patient's inhalation through the inhaler.

FIG. 7 depicts yet another embodiment of the invention providing automatic actuation of the canister to discharge a dose of medication in response to, and synchronized with, the user's inspiratory effort. An inhaler 10*c* includes a housing 12*c* having a conduit 16*c* within which an aerosol plume is created for inhalation by the user. The conduit 16*c* is shown to include the air tube 34 and the auxiliary air inlets 46. It may also include the vanes 54 of inhaler 10. Alternatively, the conduit 16*c* may be a simple straight duct with an open end for the exit of aerosolized medication. Thus, with the exception that the conduit 16*c* must adapted to provide fluid communication with a chamber 162 in housing 12*c* as discussed below, the details of the conduit 16*c* are not important to an understanding of the breath-synchronization features of the invention.

The housing 12*c* further includes a receptacle portion 14*c* which is connected to the conduit 16*c*. The receptacle portion 14*c* comprises a generally cylindrical sleeve having a longitudinal axis 108 which is oriented at an oblique angle to the longitudinal axis of the conduit 16*c*. A canister 18 resides within the receptacle portion 14*c* with its longitudinal axis aligned with the longitudinal axis of the receptacle portion 14*c*. Disposed between the receptacle portion 14*c* and the canister 18 is an inner sleeve 100. The inner sleeve 100 has an open top end 102 through which the canister 18 may be inserted, and an open bottom end 104 which is restricted such that the canister 18 cannot go through it but which nevertheless permits the hollow stem 19 of the canister to be inserted into the bore 28 of actuator and nozzle assembly 26. More specifically, the sleeve 100 adjacent bottom end 104 has inwardly extending ledges 105 which abut the cap portion 106 of the canister. The canister 18 is slidable within inner sleeve along the direction defined by the longitudinal axis 108 of receptacle portion 14*c* so as to permit the canister to be depressed toward the actuator and nozzle assembly 26 in order to actuate the canister's metering valve.

The inner sleeve 100 is also slidable within the receptacle portion 14*c* along the direction of axis 108 for the purpose of placing the canister 18 in a cocked position ready to be actuated. The receptacle portion 14*c* has four longitudinal slots 110 circumferentially spaced apart about 90 degrees, two of which receive a pair of diametrically opposite lugs or cam followers 112 extending outwardly from the outer surface of inner sleeve 100. Alternatively, the receptacle portion 14*c* may have only two slots 110 spaced 180 degrees apart and receiving the lugs 112. Thus, as the inner sleeve slides longitudinally within receptacle portion 14*c*, the lugs 112 slide longitudinally within the respective slots 110.

The inhaler includes a generally cylindrical cam ring 114 which fits over the outside of receptacle portion 14*c*. The cam ring 114 has an annular flange 116 at its lower end which extends outward beyond the outer surface of the housing so as to facilitate gripping of the cam ring 114 by the user's hand. The inner surface 118 of ring 114 has a pair of circumferentially extending recesses or cam tracks 120 formed therein approximately 180 degrees apart which extend longitudinally upward to the open top end 122 of cam ring 114. Each cam track 120 presents a generally helical surface 124 in facing relationship with one of the lugs 112 protruding outwardly from the inner sleeve 100 through slots 110. Thus, starting with the cam ring 114 in a position in which each lug 112 is in contact with the lowermost portion of the respective am track 120 (i.e., that portion of cam track 120 which is farthest from the top end 122 of cam ring 114), rotation of the cam ring 114 through the arc defined by the cam tracks 120 causes the lugs 112 to ride along the helical surfaces 124 and thereby upwardly advance the inner sleeve 100 in the longitudinal direction toward the top end 122.

This upward movement of the inner sleeve 100 draws the canister 18 upward by virtue of the ledges 105. Resisting this upward movement of the canister 18 is a compression spring 126. The spring 126 is attached to the inner surface of a removable end cap 128 which surrounds the top end 130 of the receptacle portion 14*c* and the top end 122 of the cam ring 114 to completely enclose the canister 18 in the housing. When the end cap 128 is thus installed, the spring 126 bears against the end of the canister 18, biasing the canister downward toward the actuator and nozzle assembly 26. With nothing to impede the downward movement of the canister 18, the spring 126 would move the canister downward until the discharge stem 19 were fully depressed into the canister so as to cause discharge of a metered volume of the canister contents. However, the inhaler 10*c* includes a mechanism which engages the canister to prevent this downward movement, with the mechanism being responsive to an inspiratory effort of a user exerted on the open end of the conduit 16*c* so as to disengage from the canister during the user's inhalation to allow the spring 126 to move the canister into its discharge position.

To these ends, the inhaler 10*c* includes a piston assembly 132 which is movable relative to the canister 18 along an axis 134 generally normal to the longitudinal axis 108. The piston assembly 132 includes a circular disc 136 having a shaft 138 extending centrally therethrough coaxial with axis 134 and protruding outward from both sides of the disc 136. A first portion 140 of the shaft 138 protruding from the side of disc 136 remote from the canister engages a recess 142 in a wall 144 of the housing, the recess 142 guiding the movement of the piston assembly 132 along axis 134. A second portion 146 of shaft 138 protruding from the side of disc 136 facing the canister extends through an opening 148 in receptacle portion 14*c*, terminating at an enlarged head end 150. A compression spring 152 is captive between the head end 150 and the wall of the receptacle portion 14*c*, biasing the piston assembly 132 toward the canister 18.

Figure 8:
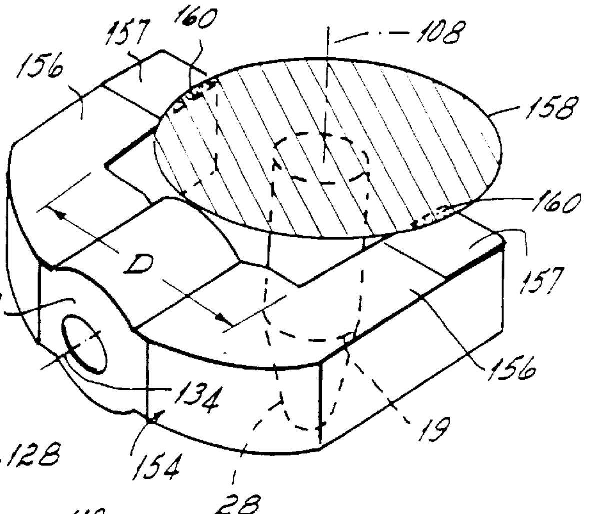
FIG. 8 is a perspective view of the trigger which engages and disengages the canister in the inhaler of FIG. 7.

A forked trigger 154 is attached to the head end 150. The trigger 154 has two spaced-apart parallel prongs 156 (FIG. 8) which extend along the direction of axis 134 to approximately the longitudinal axis 108 of the receptacle portion 14*c*. The prongs 156 are spaced apart by a distance D which is slightly smaller than the diameter of the canister neck 158 from which the discharge stem 19 protrudes, as shown schematically in FIG. 8. Thus, when the piston assembly 132 is fully extended toward the canister 18, the canister neck 158 contacts inner edge portions 160 of the prong 156, as indicated by the shaded regions in FIG. 8. However, when the piston assembly 132 is withdrawn along axis 134 away from the canister 18, the canister neck 158 clears the prongs 156 so that movement of the canister 18 toward the actuator 26 is permitted. The prongs 156 include portions 157 which slope gently away from the canister neck 158 in the direction along axis 134 toward the canister. The portions 157 reduce the amount of force required for disengagement of the trigger 154 from the canister neck 158.

Movement of the piston assembly 132 in the direction away from the canister is responsive to air pressure within a variable-volume chamber 162 within the housing. The chamber 162 is defined by the disc 136, the housing wall 144, and a flexible diaphragm 164 which connects the disc 136 to the wall 144 in a substantially air-tight manner. Advantageously, the diaphragm 164 includes a circular portion 166 which lies against the side of disc 136 facing the canister 18, and a skirt 168 which depends from the outer edge of the circular portion 166 and attaches to the housing wall 144. Further advantageously, the housing wall 144 comprises a removable cover 170 of the housing, and an edge of the skirt 168 is attached to the housing by being sandwiched between the cover 170 and the remainder of the housing. The circular portion 166 of diaphragm 164 includes a central hole through which the shaft 138 extends and which tightly surrounds the shaft 138 to provide a substantially air-tight seal therebetween.

The removable cover 170 includes a recess 172 facing the disc 136 which aligns with a passage 174 formed in a sidewall 176 of the housing. The passage 174 extends toward the open end 20*c* of conduit 16*c*. The conduit 16*c* is formed in at least two sections, a first generally cylindrical section 62*c* which includes the sidewall 176 and is connected to the end wall 24*c* through which the nozzle orifice 30 extends, and a second generally cylindrical section 74*c* which includes the air tube 34 and which connects to the first section 62*c*. The passage 174 terminates at the end of first section 62*c* which connects to second section 74*c*. A passage 178 through a sidewall 180 of the second section 74*c* is fluidly connected with and forms an extension of passage 174. The passage 178 extends into the internal passage 182 of the air tube 34. A venturi 184 is inserted into the air tube passage 182. The venturi 184 includes a restricted portion or throat 186. Air passages 188 extend through the venturi wall in the vicinity of the throat 186. The venturi 184 is disposed in passage 182 such that these air passages 188 align with the passage 178. Thus, fluid communication is provided between the venturi throat 186 and the variable-volume chamber 162 by air passages 188, passage 178 in second section 74*c*, passage 174 in first section 62*c*, and recess 172 in cover 170.

It will therefore be appreciated that when a user inhales through the open end 20*c* of conduit 16*c*, air is drawn from outside the conduit 16*c* through air tube 34 into the primary air passage of the conduit 16*c*. This air has to flow through the venturi 184, and consequently a below-atmospheric air pressure exists in the venturi throat 186. This below-atmospheric air pressure is communicated to the chamber 162, with the result that the walls of the chamber 162 are subjected to a force proportional to the pressure difference between atmospheric pressure outside the chamber 162 and the below-atmospheric pressure inside the chamber 162. Consequently, air within the chamber 162 begins to evacuate the chamber 162 through recess 172, through passages 174 and 178, through passages 188, and into the venturi throat 186, and thence through the air tube 34 into the primary air passage of the conduit 16*c*.

As the user continues to inhale through the conduit 16*c*, evacuation of air from the chamber 162 causes the volume in chamber 162 to decrease, with the result that the disc 136 and the shaft 138 begin to move toward the wall 144 against the force of the spring 152. Accordingly, the trigger 154 begins to move so as to disengage the prongs 156 from the canister neck 158. When the decrease in volume is sufficient to move the trigger 154 far enough to totally disengage the prongs 156 from the neck 158, movement of the canister 18 toward the actuator 26 is no longer impeded, and the force of spring 126 moves the canister downward so as to cause actuation of the canister's metering valve. A metered dose of aerosolized medication is thereby discharged from nozzle orifice 30 into the conduit 16*c* for inhalation by the user.

After the inhaler 10*c* has been actuated to dispense a dose of medication, it must be recocked so that it is ready to be discharged again. To this end, the user grasps the ring 114 and rotates it with respect to the housing 12*c* through the arc defined by the cam racks 120. This causes the inner sleeve 100 and canister 18 to be lifted upward against the force of spring 126. When the canister 18 is raised upwardly sufficiently to allow the trigger 154 to clear the canister neck 158, the spring 152 urges the trigger 154 toward the canister 18 so that the trigger 154 once again is in a fully extended position to engage the canister neck 158. The user then rotates the cam ring 114 back to its starting position to lower the canister 18, whereupon the canister neck 158 seats against the prongs 156 of the trigger 154. The inhaler 10*c* is then ready to be used again.

It will be appreciated that the breath-synchronization features described above provide an inhaler in which discharge of medication is automatically responsive to the user's inspiratory effort, so that the user does not have to carefully coordinate manual depression of a canister with the inhalation. Furthermore, discharge of medication does not occur immediately upon the user beginning to inhale on the open end of the device, but rather is somewhat delayed until the volume of chamber 162 has decreased enough to cause actuation. It will also be appreciated that the degree of time delay between initiation of a breath and actuation is dependent on a number of factors, the primary factors being the cross-sectional area of the chamber 162 and the spring constant of the spring 152, since a discharge of medication requires a certain minimum travel of the canister 18 to cause the discharge stem 19 to be fully depressed, and the travel is proportional to the pressure difference across the chamber times its cross-sectional area divided by the spring constant. Accordingly, the inhaler 10*c* may be designed with appropriate selection of these factors so as to achieve actuation of the canister 18 near the peak of a user's inhalation.

Moreover, the inhaler 10*c* provides breath-responsive actuation of the canister 18 which automatically adjusts to the user's rate of inhalation to discharge the medication near the peak of the inhalation, i.e., near the point at which 50 percent of the volume which the user will eventually inspire with a full inhalation has been inspired. For instance, if a user with normal lung function inhales quickly through the open end 20*c*, air will be evacuated from the chamber 162 more rapidly so as to achieve actuation in a relatively short time. Conversely, if a user with impaired lung function inhales slowly through the open end 20*c*, air will be evacuated more slowly from chamber 162 so as to achieve actuation in a relatively longer time.

The inhaler 10*c* further includes an adjustment screw 190 which extends through the housing 12*c* into the passage 174 to form a restriction within passage 174. By turning the screw 190 one direction, the screw 190 extends farther into passage 174 to increase the restriction, and by turning the screw 190 the opposite direction, it retracts to decrease the restriction. Thus, the timing of actuation of the canister 18 in relation to a particular patient's inhalation may be varied by adjusting the screw 190. Varying the screw position results in a variation in pressure difference across the walls of the variable-volume chamber 162 at a given flow rate out the open end 20*c* of conduit 16*c*. Thus, for a given flow rate out the open end 20*c* of conduit 16*c*, turning the screw 190 to increase the restriction of passage 174 will increase the time period required to evacuate the chamber 162 sufficiently to cause actuation, whereas turning the screw 190 to decrease the restriction will decrease such time period.

Figure 9:
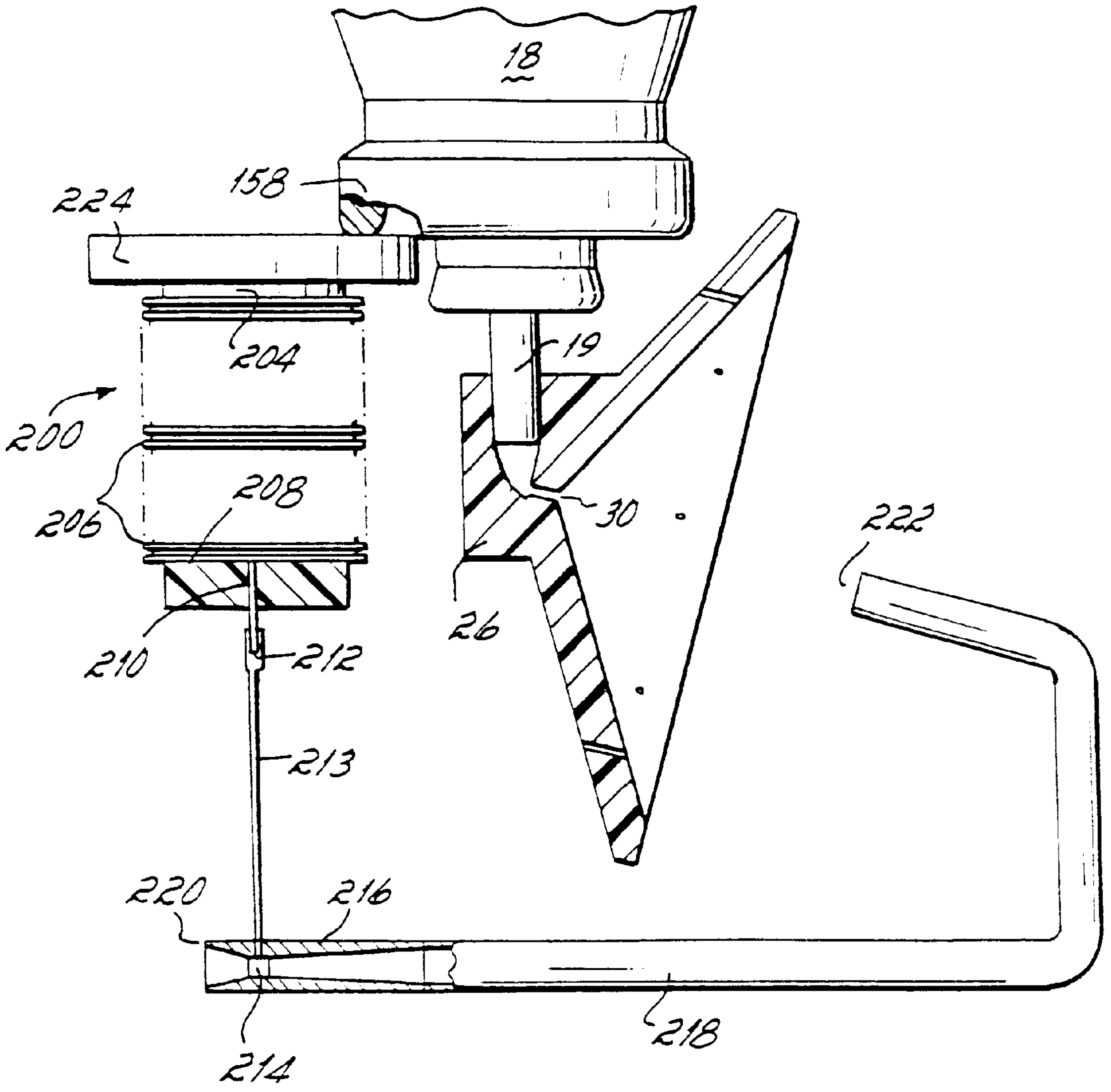
FIG. 9 is side elevational view, partly in cross-section, of yet another embodiment of the invention, showing an alternative arrangement for achieving automatic actuation of a canister responsive to a patient's breath.

FIG. 9 depicts a subassembly of yet another embodiment of an inhaler having features for automatic breath actuation of discharge. In this embodiment, the forked trigger 154 is eliminated and the diaphragm piston assembly 132 is replaced by a resiliently compressible bellows 200 which is disposed between a fixed wall of the housing (not shown) and the canister neck 158. The bellows 200 itself acts as the restraint which keeps the canister in a non-actuated position, the bellows being compressed by air pressure into a position permitting the canister to move into a discharge position.

The bellows 200 is advantageously made of stainless steel and has a blind end wall 204 at the end adjacent the canister neck 158, the end wall 204 being integrally formed with the accordion-folded side wall 206. The bellows 200 has a second end wall 208 at the end adjacent the housing wall 202, the end wall 208 also being integrally formed with the side wall 206. The second end wall 208 is pierced by a tube or needle 210 which establishes an air passage into the interior of the bellows 200. The needle 210 advantageously is a stainless steel tube similar to a hypodermic needle and is integrally affixed at one end to the end wall 208 by welding or other suitable technique. The free end 212 of the needle 210 extends is attached via an extension tube 213 to the throat 214 of a venturi 216. The venturi 216 is disposed within a tube 218 which extends from an inlet end 220 which draws air from outside the inhaler housing, to an exit end 222 which is arranged within the conduit (not shown) opposite the nozzle discharge orifice 30. The tube 218 and venturi 216 may also be formed of stainless steel.

A support/release platform 224 is attached to the blind end wall 204 of the bellows 200. The support/release platform 224 contacts the canister neck 158 throughout the range of motion undergone by the canister in moving from a rest or ready position to a discharge position. The bellows 200, via the support/release platform 224, exerts a spring force on the canister neck 158. The force of the bellows 200 acts in a direction tending to move the canister neck 158 away from the actuator 26. Additionally, as is well known, the canister 18 contains an internal spring (not shown) which acts between the canister body and the hollow outlet stem 19 in a direction tending to move the canister 18 away from the actuator 26. The spring constant of the bellows 200 is selected such that the sum of the spring force exerted by the bellows 200 and the force exerted by the internal spring is slightly greater than the force exerted by the spring 126 (FIG. 7) which exerts a force on the end of the canister 18 in the direction to tend to move the canister 18 toward the actuator 26 into its discharge position. Thus, at rest, with atmospheric pressure acting both inside and outside the bellows 200, the bellows 200 and internal spring overcome the force of the spring 126 and thereby keep the canister 18 in a ready position preventing discharge of medication therefrom.

However, when a user inhales through the outlet (not shown) of the inhaler, air is drawn through the tube 218, as previously described in connection with the inhaler 10*c*, which creates a low pressure within the throat 214 of venturi 216. This low pressure is communicated via the extension tube 213 and needle 210 to the interior of the bellows 200. As a result, the pressure within the bellows 200 is less than the atmospheric pressure which surrounds the outside of the bellows 200, and therefore there is an air pressure force exerted on the blind end wall 204 in the direction toward the housing wall 202. The sum of this air pressure force and the force of the spring 126 exceed the spring forces exerted by the bellows 200 and the canister internal spring, causing the blind end wall 204 of bellows 200 to be compressed toward the housing wall 202. By virtue of the force exerted on the canister 18 by the spring 126, the canister follows the end wall 204. With continued evacuation of air from the bellows 200, the canister 18 is moved into its discharge position. Once the user completes his inhalation and air flow through the venturi 216 ceases, air pressure is again equalized inside and outside the bellows 200, and the bellows 200 returns to its starting position, the forces of the bellows 200 and internal spring forcing the canister 18 back upward against the force of the spring 126 into the ready position. Thus, with the breath-actuation system depicted in FIG. 9, there is no need for a separate cocking system.

The bellows 200 preferably has a spring constant of about 1 pound per inch to about 12 pounds per inch, and a cross-sectional area of about 0.2 to about 0.75 square inch. Thus, a pressure differential of about one pound per square inch across the bellows 200 is sufficient to compress the bellows 200 by an amount of about 0.010 inch to about 0.080 inch. With a standard canister 18, only about 0.010 inch of relative movement is required between the discharge stem 19 and the canister body in order to cause discharge. Accordingly, the venturi 216 must be sized to create a gage pressure within the throat 214 of about one pound per square inch.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. For example, while the inhalers which are illustrated and described have the venturi inlet in communication with ambient air via a passage through the conduit wall, the venturi inlet may alternatively draw air through one of the auxiliary air inlets 46 in the end wall 24, or through any arrangement having the venturi inlet outside the primary air passage defined by the inhaler conduit. Additionally, the stainless steel bellows 200 of FIG. 8 may advantageously be used in the inhaler configuration depicted in FIG. 7, with the bellows 200 replacing the piston assembly 132 and the blind end wall 204 of the bellows 200 being attached to the forked trigger 154, and the spring 152 being eliminated by virtue of the resiliency of the bellows 200. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An aerosol flow control apparatus providing automatic discharge of medication responsive to an inspiratory effort of a user, the apparatus comprising:

a pressurized canister of medication including a canister body and a hollow discharge stem which is movable with respect to the canister body between an inoperative position in which discharge of medication is prevented and an operative position in which medication is discharged through the discharge stem;

a housing adapted to support the canister and permit movement thereof between a first position in which the discharge stem is in the inoperative position to a second position in which the discharge stem is in the operative position, the housing further defining a primary air passage including an outlet through which a user can inhale and also defining a secondary air passage extending between the primary air passage and ambient air outside the primary air passage, the secondary air passage including a venturi having a throat;

a variable-volume device supported within the housing and including a wall which is movable with respect to the housing, the variable-volume device defining a variable-volume chamber therein in fluid communication with the venturi throat;

a canister restraint affixed to the movable wall of the variable-volume device, the canister restraint being movable with the movable wall from a rest position in which the canister is in the first position and relative movement between the canister body and discharge stem is prevented, to a discharge position in which the canister is free to move into the second position;

a resilient member which urges the canister into the second position upon movement of the canister restraint into its discharge position; and the variable-volume chamber being in fluid communication with the primary air passage, whereby inhalation of a user through the outlet causes air to be drawn through the venturi throat thereby creating a low pressure in the throat which is communicated to the variable-volume chamber, the low pressure causing air to be evacuated from the chamber and thereby cause the movable wall to move the canister restraint into the discharge position.

2. The aerosol flow control apparatus of claim 1, wherein the venturi throat is connected to the chamber by a third air passage within the housing, and further comprising an adjustment device which may be selectively positioned to selectively vary the flow rate through the third air passage at a given flow rate through the primary air passage, thereby varying the timing of medication discharge in relation to the inhalation cycle of a user.

3. The aerosol flow control apparatus of claim 1, wherein the variable-volume device comprises a piston which is sealingly connected to a wall of the housing by a flexible diaphragm, and the canister restraint includes a member which is attached to the piston and which in the rest position intrudes into the path traveled by the canister between the first and second positions so as to prevent the canister from moving into the second position, evacuation of air from within the chamber of the variable-volume device causing the piston to move toward the housing wall and thereby withdraw the member into the discharge position permitting the canister to move into the second position.

4. The aerosol flow control apparatus of claim 1, wherein the housing comprises a main body portion which receives the canister, and an end cap which covers the end of the canister opposite from the end with the discharge stem and which engages the main body portion to prevent inadvertent removal therefrom, the resilient member comprising a compression spring between an inner surface of the end cap and the canister such that the spring bears against the canister when the end cap is engaged with the main body portion.

5. The aerosol flow control apparatus of claim 3, wherein the main body portion includes a generally cylindrical receptacle having a longitudinal axis and defining a generally cylindrical recess in which the canister resides, and further comprising a cocking device including:

an inner sleeve which surrounds the canister within the receptacle, the inner sleeve and canister being slidable together as a unit within the receptacle along the longitudinal axis, the inner sleeve further including at least one pin extending outwardly from an outer surface thereof through a slot in the receptacle; and a cocking ring which surrounds the receptacle and has a surface which engages the at least one pin, the cocking ring being movable with respect to the receptacle so as to move the pin in the direction defined by the longitudinal axis toward the end cap so as to draw the inner sleeve and canister upward and thereby move the canister into a cocked position which permits the canister restraint to move into its rest position, thereby readying the apparatus for actuation in response to the inspiratory effort of a user.

6. The aerosol flow control apparatus of claim 1, wherein the variable-volume device comprises a resiliently compressible bellows, the bellows being disposed between a neck of the canister and a wall of the housing which faces the canister neck, the movable wall being an end wall of the bellows, the canister restraint being affixed to the end wall and contacting the canister neck, the bellows being compressible toward the housing wall in a direction substantially parallel to the direction in which the canister moves from the first position to the second position, the bellows being adapted to exert a spring force on the canister tending to urge the canister toward the first position, the spring force exceeding the force exerted on the canister by the resilient member by a predetermined amount which is selected such that when a user inhales through the outlet of the housing, the pressure force exerted on the end wall of the bellows by the difference between atmospheric pressure outside the bellows and the low pressure inside the bellows exceeds the predetermined amount, thereby causing the end wall to compress the bellows toward the housing wall and move the canister restraint into the discharge position such that the canister is moved into the second position by the resilient member.

7. In an aerosol delivery apparatus which houses a medication-containing canister having a canister body and a hollow outlet stem movable with respect to the canister body between an inoperative position in which discharge of medication is prevented and an operative position in which medication is discharged through the outlet stem, with the canister being movable within the apparatus between a first position in which the outlet stem is in the inoperative position and a second position in which the outlet stem is in the operative position, the apparatus including a housing defining a primary air passage having an outlet through which a user can inhale, a method of synchronizing discharge of medication from the canister with an inspiratory effort of a user through the outlet, the method comprising:

placing the canister in the first position;

preventing movement of the canister into the second position by a canister restraint which engages the canister to prevent said movement and which is movable in response to below-atmospheric air pressure within a variable-volume device arranged within the housing, the variable-volume device defining an air chamber therein, the canister restraint being movable to permit the canister to move into the second position upon a predetermined decrease in volume of the air chamber;

urging the canister toward the second position;

upon a user inhaling through the outlet, drawing air through a secondary air passage arranged within the housing, the secondary air passage extending from the primary air passage to ambient air outside the primary air passage; and at least during the drawing step, providing fluid communication between the secondary air passage and the air chamber so as to communicate a below-atmospheric air pressure to the air chamber and thereby cause the chamber volume to decrease, whereby the canister restraint moves to permit said movement of the canister into the second position to discharge medication when the predetermined decrease in chamber volume is reached.

8. The method of claim 7, wherein the providing step comprises providing fluid communication between a throat portion of the secondary air passage and the variable-volume chamber to evacuate air therefrom, the throat portion having a reduced cross-sectional flow area relative to the remainder of the secondary air passage such that the air pressure in the throat portion is lower than the air pressure in the remainder of the secondary air passage when air is flowing therethrough.

* * * * *

UNITED STATES PATENT AND TRADEMARK OFFICE
CERTIFICATE OF CORRECTION

PATENT NO. : 6,095,141
DATED : August 1, 2000
INVENTOR(S) : Thomas Alex Armer et al.

It is certified that error appears in the above-identified patent and that said Letters Patent is hereby corrected as shown below:

Column 1,
Line 44, "exists" should read -- exits --;
Line 54, "does" should read -- dose --; and
Line 60, "does" should read -- dose --.

Column 2,
Line 53, "he" should read -- the --; and
Line 64, "he" should read -- the --.

Column 3,
Line 37, "does" should read -- dose --.

Column 4,
Line 6, "atone" should read -- at one --.

Column 7,
Line 11, "does" should read -- dose --.

Column 9,
Line 61, "36*a*is" should read -- 36*a* is --; and
Line 66, "10*a*shown" should read -- 10*a* shown --.

Column 10,
Line 17, "cross sectional" should read -- cross-sectional --; and
Line 19, "cross sectional" should read -- cross-sectional --.

UNITED STATES PATENT AND TRADEMARK OFFICE

CERTIFICATE OF CORRECTION

PATENT NO. : 6,095,141
DATED : August 1, 2000
INVENTOR(S) : Thomas Alex Armer et al.

It is certified that error appears in the above-identified patent and that said Letters Patent is hereby corrected as shown below:

<u>Column 11,</u>
Line 7, "must" should read -- must be --; and
Line 61, "am" should read -- cam --.

Signed and Sealed this

Fifth Day of March, 2002

*Attest:*

JAMES E. ROGAN

*Attesting Officer*

*Director of the United States Patent and Trademark Office*